United States Patent [19]

Okorodudu

[11] 4,252,660

[45] Feb. 24, 1981

[54] REACTION PRODUCTS OF ORGANOPHOSPHORUS HALIDES WITH INORGANIC THIOCYANATES AS LOAD-CARRYING ADDITIVES IN LUBRICATING OIL COMPOSITIONS

[75] Inventor: Abraham O. M. Okorodudu, West Deptford, N.J.

[73] Assignee: Mobil Oil Corporation, New York, N.Y.

[21] Appl. No.: 97,065

[22] Filed: Nov. 23, 1979

[51] Int. Cl.$^3$ .............................................. C10M 1/48
[52] U.S. Cl. .................................. 252/46.7; 252/32.5; 260/454; 260/940
[58] Field of Search .............................. 252/46.7, 32.5

[56] References Cited

U.S. PATENT DOCUMENTS

| 2,256,380 | 9/1941 | Dickey | 252/32.5 X |
| 2,494,284 | 1/1950 | Cassaday et al. | 252/46.7 X |
| 2,733,207 | 1/1956 | Otto | 252/46.7 X |
| 2,874,120 | 2/1959 | Watson et al. | 252/32.5 |
| 2,882,228 | 4/1959 | Watson et al. | 252/32.5 |
| 3,328,495 | 6/1967 | Anders et al. | 252/46.7 X |
| 4,081,445 | 3/1978 | Hermans | 252/46.7 X |

*Primary Examiner*—Andrew Metz
*Attorney, Agent, or Firm*—Charles A. Huggett; Michael G. Gilman; Howard M. Flournoy

[57] ABSTRACT

Reaction products of selected inorganic thiocyanates and alkyl or aryl phosphorus halides provide additive compounds which impart excellent antiwear and load-carrying protection to lubricant base stocks in which they are incorporated.

13 Claims, No Drawings

REACTION PRODUCTS OF ORGANOPHOSPHORUS HALIDES WITH INORGANIC THIOCYANATES AS LOAD-CARRYING ADDITIVES IN LUBRICATING OIL COMPOSITIONS

BACKGROUND OF THE INVENTION

1. Field of the Invention

This invention relates to lubricant compositions having excellent antiwear and load-carrying properties. More particularly it relates to improving such properties of a lubricant by adding a minor effective amount of the reaction products of certain organophosphorus halides and sodium, potassium or ammonium thiocyanates thereto.

2. Description of the Prior Art

Lubricants are subject to heavy stresses that can affect their antiwear and load carrying ability. Thus, there has been considerable effort to discover classes of compounds that will aid in retaining or in improving these important properties.

For example, sulfur compounds have been used for the purpose, as is taught in U.S. Pat. No. 3,697,499. Unfortunately, the presence of sulfur in lubricants may cause severe metal corrosion, especially of copper. To overcome this, special processes have been used to moderate the effect of sulfur, as in U.S. Pat. No. 3,697,499, or other additive materials have been used, among them certain phosphorus compounds. U.S. Pat. No. 3,663,439, for instance, discloses lubricating oils whose extreme pressure properties have been improved by adding thereto a reaction product involving a trihydrocarbyl phosphate. However no references are known to applicant (patent or literature) wherein the antiwear and load-carrying properties of lubricants are improved by the addition of the about described reaction products.

SUMMARY OF THE INVENTION

This invention provides a lubricant composition comprising a lubricant selected from mineral or synthetic oils of lubricant viscosity and minor antiwear/load-carrying amounts of a product prepared by reacting organophosphorus halides and inorganic thiocyanates.

The organophosphorus halides useful herein have the general formula:

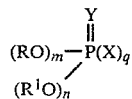

where Y is 0 or S, $m=3-(n+q)$, $n=3-(m+q)$ and $q=3-(n+m)$ but not zero, and X is a halide selected from chloride, bromide, or iodide and where R and $R^1$ may be the same or different and each is a hydrocarbyl group containing from 1 to about 36 carbon atoms. Preferred are alkyl groups having from 4 to 12 carbon atoms and alkaryl groups or arylalkyl groups containing phenyl, naphthyl and anthryl radicals, the alkyl substituents thereof containing from 1 to about 20 carbon atoms.

The precise nature of the product produced in accordance with the invention is not known but a significant part of the reaction product is formed in accordance with the following equation:

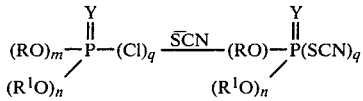

where R and $R^1$ and m, n and q have the above meanings.

The reaction temperature is usually ambient or at higher temperatures to 200° C. or from ambient to the reflux temperature of the solvent used. A solvent is generally used. Criteria for selecting it include solubility of the reactants and products therein and ease of removal from the final products. Suitable solvents include toluene, dimethoxyethane, pyridine, dimethylformamide (DMF) etc.

The products in accordance with this invention as indicated above are generally made by reacting molar amounts of organophosphorous halides, e.g., chloride, bromide or iodide with at least a stoichiometric equivalent molar amounts of inorganic thiocyanates such as ammonium, sodium or potassium.

The organophosphorus halide is generally added dropwise to a mixture containing excess inorganic thiocyanate and solvent. Following the exothermic reaction the mixture is refluxed for about an hour, cooled and treated with a solvent/water mixture. Thereafter the organic layer is stripped of solvent and the residue collected.

Lubricants which are improved by the reaction products of this invention are mineral and synthetic lubricating oils, mixtures thereof, greases prepared therefrom and various functional fluids, such as hydraulic fluids. The mineral oils will be understood to include not only paraffinic members, but also naphthenic members. By synthetic oils are meant synthetic hydrocarbons, polyalkylene oxide oils, polyacetals, polysilicones and the like, as well as synthetic ester oils. Included among the latter type are those esters made from monohydric alcohols and polycarboxylic acids, such as 2-ethylhexylazelate and the like. Also included are those esters made from polyhydric alcohols and aliphatic monocarboxylic acids. Those of this group are especially important and in this group are found esters prepared from (1) the trimethylols, such as the ethane, propane and butane derivatives thereof and 2,2-disubstituted propane diols and (2) the pentaerythritols reacted with aliphatic monocarboxylic acids containing from about 4 to 9 carbon atoms. Mixtures of these acids may be used to prepare the esters. Preferred among the esters are those made from pentaerythritol and a mixture of $C_5$–$C_9$ acids.

As has been indicated, the reaction products disclosed herein are useful as antiwear and load carrying agents. When so used, they may be added in amounts sufficient to impart such properties to the lubricant. Generally, the useful amount will range from about 0.25% to about 10% by weight, preferably from about 1% to about 5%, by weight of the total composition.

Having discussed the invention in broad and general terms, the following examples are offered to illustrate it. It is to be understood that they are merely illustrative and are not intended to limit the scope of the invention or of the appended claims.

EXAMPLE 1

The reaction product of di(nonylphenyl) phosphorochloridite and ammonium thiocyanate was prepared as follows:

To a slurry of ammonium thiocyanate 76 g (1 mole) in 250 ml of toluene at ambient temperature, was added, dropwise, with stirring, 101 g (0.2 moles) of di(nonylphenyl) phosphorochloridite. Following the exothermic reaction, the reaction mixture was refluxed for 1 hr. and the external heat removed. After cooling, the mixture was treated with benzene and water. The organic layer was further washed with water, dried over anhydrous $MgSO_4$ and stripped of solvent to give the desired product.

EXAMPLE 2

The reaction product of nonylphenyl phosphorodichloridite and ammonium thiocyanate was prepared essentially as outlined in Example 1 using the same molar quantities of reactants.

EXAMPLE 3

The reaction product of di(nonylphenyl) phosphorochloridate and ammonium thiocyanate was prepared as follows:

Di(nonylphenyl) phosphorochloridate (0.2 moles) was added dropwise to a slurry of 1 mole of ammonium thiocyanate in 200 ml of toluene. After the exothermic reaction, the mixture was refluxed for 1 hr., cooled and filtered. The solids were washed several times with toluene and the filtrate was washed with water, dried over anhydrous $MgSO_4$ and stripped of solvent to give the desired product.

EXAMPLE 4

The reaction product of n-octyl phosphorodichloridite and potassium thiocyanate was prepared as follows:

n-Octyl phosphorodichloridite, 46 g (0.2 moles) was added dropwise at ambient temperature to a stirred slurry of potassium thiocyanate (1 mole), 300 ml of pyridine and 250 ml of benzene. After the addition and the resulting exothermic reaction, the mixture was refluxed for 6 hrs.; cooled and treated with benzene and dilute HCl. The organic portion was washed with water and dried over anhydrous $MgSO_4$ and stripped of solvent to give the desired product which was then filtered through "hi flo" filter aid.

EXAMPLE 5

The reaction product of dibutyl phosphorochloridite and ammonium thiocyanate was prepared essentially as outlined in Example 1, using the same molar quantities of reactants.

EXAMPLE 6

The reaction product of butyl phosphorodichloridite and ammonium thiocyanate was prepared essentially as outlined in Example 1, using the same molar quantities of reactants.

EXAMPLE 7

The reaction product of dioctyl phosphorochloridite and ammonium thiocyanate was prepared essentially as outlined in Example 1, using the same molar quantities of reactants.

EXAMPLE 8

The reaction of Example 7 was repeated, using sodium thiocyanate instead of ammonium thiocyanate.

Products of the above Examples were tested in the 4-Ball Wear Test using a modified 4-Ball machine. In this test, three stationary balls are placed in a lubricant cup and a lubricant containing the additive to be tested is added thereto. A fourth ball is placed on a chuck, mounted on a device which can be used to spin the ball at known speeds and loads.

100 cc of lubricating oil consisting of 80 parts of solvent-refined Mid-Continent paraffinic 150–160 bright mineral oil and 20 parts of furfural refined Mid-Continent 200/210 neutral mineral oil was used as the test lubricant. The products exemplified in Examples 1 through 8 were also tested in synthetic base stock. The base stock contained 0.5% by weight of the product of the specified example. The following table summarizes the results.

TABLE 1

4-BALL WEAR TEST SCAR DIAM. (mm)
½" BALLS, 52100 STEEL, 60 KG, 30 MIN.

| Example No. | Mineral Oil (80/20) Base Stock | | | | | | Drew Ester Base Stock | | | | | |
|---|---|---|---|---|---|---|---|---|---|---|---|---|
| | Conc. Wt. % | Temp. °F. | SPEED (RPM) | | | | Conc. Wt. % | Temp. °F. | SPEED (RPM) | | | |
| | | | 500 | 1,000 | 1,500 | 2,000 | | | 500 | 1,000 | 1,500 | 2,000 |
| None (Base Lubricant) | | Room | 0.50 | 1.60 | 0.88 | 2.34 | | Room | 0.80 | 1.0 | 1.10 | 1.90 |
| | | 200 | 0.60 | 1.06 | 1.86 | 2.23 | | 200 | 1.0 | 1.10 | 2.40 | 2.30 |
| | | 390 | 1.0 | 1.31 | 2.06 | — | | 390 | 1.10 | 1.40 | 2.0 | 2.50 |
| 1 | 0.5 | Room | 0.30 | 0.30 | 0.40 | 0.45 | 0.5 | Room | 0.40 | 0.40 | 0.40 | 1.50 |
| | | 200 | 0.30 | 0.30 | 0.40 | 0.40 | | 200 | 0.30 | 0.40 | 0.40 | 1.50 |
| | | 390 | 0.40 | 0.50 | 0.50 | 0.50 | | 390 | 0.40 | 0.60 | 1.50 | 0.60 |
| 2 | 0.5 | Room | 0.30 | 0.30 | 0.30 | 0.30 | 0.5 | Room | 0.40 | 0.40 | 0.40 | 1.50 |
| | | 200 | 0.30 | 0.30 | 0.40 | 0.40 | | 200 | 0.30 | 0.40 | 0.40 | 1.60 |
| | | 390 | 0.40 | 0.40 | 0.40 | 0.50 | | 390 | 0.40 | 0.50 | 0.70 | 1.30 |
| 3 | 0.5 | Room | 0.30 | 0.30 | 0.30 | 0.40 | 0.5 | Room | 0.50 | 0.40 | 0.50 | 1.30 |
| | | 200 | 0.30 | 0.30 | 0.50 | 0.50 | | 200 | 0.40 | 0.40 | 0.60 | 1.50 |
| | | 390 | 0.40 | 1.10 | 0.40 | 1.60 | | 390 | 0.40 | 0.90 | 1.40 | 1.50 |
| 4 | 0.5 | Room | 0.40 | 0.40 | 0.40 | 0.40 | 0.5 | Room | 0.40 | 0.40 | 1.0 | 1.40 |
| | | 200 | 0.40 | 0.30 | 0.40 | 0.40 | | 200 | 0.40 | 0.40 | 0.40 | 1.40 |
| | | 390 | 0.30 | 0.40 | 0.70 | 0.70 | | 390 | 0.40 | 0.50 | 1.80 | 1.40 |
| 5 | 0.5 | Room | 0.30 | 0.30 | 0.30 | 0.30 | 0.5 | Room | 0.40 | 0.40 | 0.50 | 0.60 |
| | | 200 | 0.40 | 0.40 | 0.40 | 0.40 | | 200 | 0.40 | 0.50 | 0.50 | 0.50 |
| | | 390 | 0.40 | 0.30 | 0.40 | 0.50 | | 390 | 0.40 | 0.40 | 0.60 | 0.60 |
| 6 | 0.5 | Room | 0.30 | 0.40 | 0.40 | 0.40 | 0.5 | Room | 0.40 | 0.40 | 0.50 | 0.50 |
| | | 200 | 0.30 | 0.30 | 0.30 | 0.40 | | 200 | 0.40 | 0.40 | 0.50 | 1.30 |
| | | 390 | 0.40 | 0.40 | 0.40 | 0.40 | | 390 | 0.40 | 0.40 | 0.60 | 1.40 |
| 7 | 0.5 | Room | 0.30 | 0.30 | 0.30 | 0.30 | 0.5 | Room | 0.40 | 0.40 | 0.40 | 1.10 |

TABLE 1-continued

| | 4-BALL WEAR TEST SCAR DIAM. (mm) 1/2" BALLS, 52100 STEEL, 60 KG, 30 MIN. | | | | | | | | | | | |
|---|---|---|---|---|---|---|---|---|---|---|---|---|
| | Mineral Oil (80/20) Base Stock | | | | | | Drew Ester Base Stock | | | | | |
| | Conc. | Temp. | SPEED (RPM) | | | | Conc. | Temp. | SPEED (RPM) | | | |
| Example No. | Wt. % | °F. | 500 | 1,000 | 1,500 | 2,000 | Wt. % | °F. | 500 | 1,000 | 1,500 | 2,000 |
| 8 | 0.5 | 200 | 0.40 | 0.40 | 0.30 | 0.40 | 0.5 | 200 | 0.30 | 0.30 | 0.30 | 1.50 |
| | | 390 | 0.30 | 0.40 | 0.60 | 0.70 | | 390 | 0.40 | 0.50 | 1.50 | 1.60 |
| | | Room | 0.30 | 0.40 | 0.40 | 0.50 | | Room | 0.40 | 0.40 | 0.40 | 0.40 |
| | | 200 | 0.30 | 0.40 | 0.40 | 0.50 | | 200 | 0.40 | 0.40 | 0.40 | 0.40 |
| | | 390 | 0.30 | 0.40 | 0.60 | 0.70 | | 390 | 0.40 | 0.60 | 0.70 | 0.70 |

I claim:

1. A lubricant composition comprising a major proportion of a mineral oil, a synthetic oil or greases thereof and a minor proportion sufficient to impart antiwear and load-carrying characteristics thereto of a product prepared by reacting from about 0.2 mole to about 1 mole of an organophosphorus halide; having the following generalized formula:

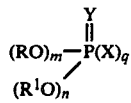

where $m=3-(n+q)$, $n=3-(m+q)$ and $q=3-(n+m)$ but not zero, and Y is O or S, X is a halide selected from chloride, bromide or iodide and R and $R^1$ may be the same or different and each is a hydrocarbyl group containing from 1 to about 36 carbon atoms selected from alkyl groups having from about 4 to 12 carbon atoms and alkaryl groups comprised of phenyl, naphthyl or anthryl with the alkyl substituents thereof containing from 1 to about 20 carbon atoms; with from about 1 to about 5 moles of an inorganic thiocyanate selected from sodium, potassium or ammonium thiocyanates.

2. The composition of claim 1 wherein the thiocyanate is ammonium thiocyanate and the organophosphorus halide is an organophosphorus chloride.

3. The composition of claim 2 wherein the organophosphorus halide is di(nonylphenyl) phosphorochloridate.

4. The composition of claim 2 wherein the organophosphorus halide is nonylphenyl phosphorochloridite.

5. The composition of claim 2 wherein the organophosphorus halide is di(nonylphenyl) phosphorochloridite.

6. The composition of claim 2 wherein the organophosphorus halide is n-octyl phosphorochlorodite.

7. The composition of claim 2 wherein the organophosphorus halide is dibutyl phosphorochlorodite.

8. The composition of claim 2 wherein the organophosphorus halide is butyl phosphorochlorodite.

9. The composition of claim 2 wherein the organophosphorus halide is dioctyl phosphorochlorodite.

10. The composition of claim 1 wherein the organophosphorus halide is n-octyl phosphorochlorodite and the thiocyanate is potassium thiocyanate.

11. The composition of claim 2 wherein the organophosphorus halide is dioctyl phosphorochlorodite and the thiocyanate is sodium thiocyanate.

12. The composition of claim 1 wherein the lubricant is a mineral lubricating oil or a grease prepared therefrom.

13. The composition of claim 1 wherein the lubricant is a synthetic lubricating oil or a grease prepared therefrom.

* * * * *